United States Patent
Tsukada et al.

(10) Patent No.: US 11,666,244 B2
(45) Date of Patent: Jun. 6, 2023

(54) FOOT SOLE PRESSURE MEASUREMENT INSTRUMENT, INFORMATION PROVISION DEVICE, AND INFORMATION PROVISION METHOD

(71) Applicants: NIPPON TELEGRAPH AND TELEPHONE CORPORATION, Tokyo (JP); THE UNIVERSITY OF TOKYO, Tokyo (JP)

(72) Inventors: Shingo Tsukada, Atsugi (JP); Hiroshi Nakashima, Atsugi (JP); Nahoko Kasai, Atsugi (JP); Hideo Hatta, Tokyo (JP)

(73) Assignees: NIPPON TELEGRAPH AND TELEPHONE CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 67 days.

(21) Appl. No.: 16/633,320

(22) PCT Filed: Aug. 13, 2018

(86) PCT No.: PCT/JP2018/030207
§ 371 (c)(1),
(2) Date: Jan. 23, 2020

(87) PCT Pub. No.: WO2019/035444
PCT Pub. Date: Feb. 21, 2021

(65) Prior Publication Data
US 2020/0146592 A1 May 14, 2020

(30) Foreign Application Priority Data
Aug. 16, 2017 (JP) .............................. JP2017-157049

(51) Int. Cl.
*A61B 5/103* (2006.01)
*A61B 5/00* (2006.01)
*A63B 24/00* (2006.01)

(52) U.S. Cl.
CPC .......... *A61B 5/1038* (2013.01); *A61B 5/6807* (2013.01); *A61B 5/742* (2013.01); *A63B 24/0062* (2013.01); *A63B 2225/52* (2013.01)

(58) Field of Classification Search
CPC ..... A43B 3/0005; A43B 313/12; A43B 13/14; A43B 13/122; A43B 13/125;
(Continued)

(56) References Cited

U.S. PATENT DOCUMENTS 5,469,740 A * 11/1995 French ................. A61B 5/4023
482/901
8,676,541 B2 * 3/2014 Schrock ............... A61B 5/6807
702/188

(Continued)

FOREIGN PATENT DOCUMENTS

CN 102319503 A 1/2012
CN 103340735 A 10/2013
(Continued)

OTHER PUBLICATIONS

C3FIT In-Pulse, [Online], Internet<URL:http://www.goldwin.co.jp/ec/contents/c3fit/inpulse/about.html>, Goldwin Inc., 2016.
(Continued)

*Primary Examiner* — David J. McCrosky
(74) *Attorney, Agent, or Firm* — Harness, Dickey & Pierce, P.L.C.

(57) ABSTRACT

A foot sole pressure measurement instrument includes a measurement unit which is installed on a foot sole part of a
(Continued)

subject and measures a pressure applied to the foot sole part of the subject, and an output unit configured to output data of the measured pressure.

5 Claims, 8 Drawing Sheets

(58) Field of Classification Search
CPC ... A43B 17/1405; A43B 13/386; A43B 7/084; A43B 7/087; A43B 7/088; A61B 2503/10; A61B 2562/0247; A61B 5/1038; A61B 5/112; A61B 5/1124; A61B 5/4866; A61B 5/6807; A61B 5/742; A63B 2024/0065; A63B 2024/0093; A63B 2071/065; A63B 2071/0675; A63B 22/0023; A63B 22/02; A63B 2220/30; A63B 2220/51; A63B 2220/56; A63B 2220/836; A63B 2225/52; A63B 2230/201; A63B 24/0062; A63B 69/0035
See application file for complete search history.

(56) References Cited

U.S. PATENT DOCUMENTS

| | | | |
|---|---|---|---|
| 2007/0032706 A1* | 2/2007 | Kamath | A61B 5/726 600/300 |
| 2007/0151348 A1* | 7/2007 | Zdeblick | A61B 5/0215 73/708 |
| 2009/0137366 A1 | 5/2009 | Hirata et al. | |
| 2010/0152619 A1* | 6/2010 | Kalpaxis | A63F 13/06 600/592 |
| 2011/0009777 A1* | 1/2011 | Reichow | A63B 23/025 600/595 |
| 2011/0140897 A1 | 6/2011 | Purks et al. | |
| 2012/0092169 A1* | 4/2012 | Kaiser | A61B 5/6807 340/573.1 |

FOREIGN PATENT DOCUMENTS

| | | |
|---|---|---|
| CN | 105078463 A | 11/2015 |
| CN | 106618579 A | 5/2017 |
| CN | 107174252 A * | 9/2017 |
| CN | 107281700 B * | 8/2019 |
| JP | H10-005369 A | 1/1998 |
| JP | 2005-156531 A | 6/2005 |
| JP | 2007-275283 A | 10/2007 |
| JP | 2011-524207 A | 9/2011 |
| JP | 2015-206601 A | 11/2015 |
| WO | WO-2009152456 A2 | 12/2009 |
| WO | WO-2019022533 A1 | 1/2019 |

OTHER PUBLICATIONS

International Search Report (in English and Japanese) regarding PCT/JP2018/030207, dated Nov. 6, 2018 ISA/JP.

Shu, Lin et al., "In-Shoe Plantar Pressure Measurement And Analysis System Based On Fabric Pressure Sensing Array", IEEE Transactions On Information Technology In Biomedicine, IEEE Service Center, Los Alamitos, CA, US, vol. 14, No. 3, May 1, 2010, pp. 767-775, XP011345692, ISSN: 1089-7771, DOI: 10.1109/TITB. 2009.2038904.

Emborg, Jonas et al., "Withdrawal reflexes examined during human gait by ground reaction forces: site and gait phase dependency", Medical & Biological Engineering & Computing, Springer, Berlin, DE, vol. 47, No. 1, Oct. 1, 2008, pp. 29-39, XP019835300, ISSN: 1741-0444.

Kawsar, Ferdaus et al., "Remote Monitoring Using Smartphone Based Plantar Pressure Sensors: Unimodal and Multimodal Activity Detection", In: "12th European Conference on Computer Vision, ECCV 2012", Dec. 27. 2014, Springer Berlin Heidelberg, Berlin, Germany 031559, XP055727805, ISSN: 0302-9743, ISBN: 978-3-642-36741-0, vol. 8456, pp. 138-146, DOI: 10.1007/978-3-319-14424-5_15.

* cited by examiner

| | | v=200m/min | | | v=225m/min | | |
|---|---|---|---|---|---|---|---|
| | | PITCH (TIMES/min) | STRIDE (TIMES/cm) | BLOOD LACTATE CONCENTRATION (mmol/l) | PITCH (TIMES/min) | STRIDE (TIMES/cm) | BLOOD LACTATE CONCENTRATION (mmol/l) |
| MONTH:○ YEAR:20XX | FLAT GROUND | 183 | 109 | 0.9 | 186 | 121 | 0.7 |
| MONTH:□ YEAR:20XX | FLAT GROUND | – | – | 0.8 | 188 | 114 | 0.7 |
| MONTH:△ YEAR:20XX | SLOPE | 189 | 103 | 2 | 192 | 113 | 3.4 |

FOOT SOLE PRESSURE MEASUREMENT INSTRUMENT, INFORMATION PROVISION DEVICE, AND INFORMATION PROVISION METHOD

CROSS-REFERENCE TO RELATED APPLICATIONS

This application is a 371 U.S. National Phase of International Application No. PCT/JP2018/030207, filed on Aug. 13, 2018, which claims priority to Japanese Application No. 2017-157049, filed on Aug. 16, 2017. The entire disclosures of the above applications are incorporated herein by reference.

TECHNICAL FIELD

The present invention relates to a foot sole pressure measurement instrument, an information provision device, and an information provision method.

Priority is claimed on Japanese Patent Application No. 2017-157049, filed Aug. 16, 2017, the content of which is incorporated herein by reference.

BACKGROUND ART

In recent years, it has been noticed that exercise has a great effect on improvement of physical ability and health enhancement. Particularly, in the field of competition sports, more efficient exercise training and improvement of competitiveness are expected according to new viewpoints or methods. In addition, also in the medical field, walking rehabilitation is an important subject, and apparatuses that support safe and efficient walking training are required.

Recently, technological innovations such as wearable devices or smartphones including various types of sensors and interfaces have advanced. With such an apparatus, it is possible to introduce a new technology that targets exercise (for example, refer to Non-Patent Document 1). Poor physical condition, fatigue, and worsening of chronic diseases cause a balance or rhythm of running exercise to deteriorate. Therefore, it is possible to prevent accidents due to overwork and poor physical condition or occurrence of major failures by monitoring a situation of running exercise, detecting an abnormal fluctuation in the balance or rhythm of running exercise based on data acquired from a sensor, and intervening sooner when the balance or rhythm of running exercise has deteriorated.

Information detected by a wearable sensor ranges variously from a heartbeat, myoelectricity, and electroencephalography to body temperature and the like, but since a foot sole pressure among them allows direct evaluation of a state of running or walking of a runner, and conversion of the state into load information such as a lactate concentration, the foot sole pressure is very important information for runners.

On the other hand, it is necessary to perform maintenance of a posture and walking exercise by mobilizing the leg strength on a healthy side and the muscular strength of the whole body such as an upper limb or the trunk while supporting an affected side (paralyzed side or affected limb) using braces and support devices in walking training rehabilitation. In progress in walking training, there are large individual differences in conditions of a disease, muscular strength, motivation, and the like, and there is a need for apparatuses that measure a gait objectively and conveniently. That is, it is useful to evaluate a gait during exercise rehabilitation based on change in a peak value of a foot sole pressure, a walking rhythm, or a speed.

In addition, determination of whether a patient may shift to independent walking by removing a support device such as a suspension device or a walking device from the patient largely depends on subjective evaluation. It is desired, however, to introduce an objective evaluation indicator from the point of view of reducing the fall risk of a patient. Furthermore, in recent years, walking training devices using robot technology have been developed, and technology for analysis of data of a foot sole pressure and features of a gait is regarded as important to ascertain an interrelationship between support exercise using a machine and voluntary exercise on a health side in an exercise on an affected side and progress in the rehabilitation.

DOCUMENTS OF THE PRIOR ART

[Non Patent Document]

[Non Patent Document 1]
"C3fit IN-pulse" [online]. Internet
<URL:http://www.goldwin.co.jp/ec/contents/c3fit/in-pulse/about.html>

SUMMARY OF INVENTION

Problems to be Solved by the Invention

However, due to differences in foot size and skeleton size, for example, even if subjects have the same size of shoes and socks, locations on the foot to which a maximum pressure is applied may not be the same. In particular, a lower edge of an epiphyseal portion of a heel bone and a lower edge of an epiphyseal portion of a metatarsal bone are important as points of action of a floor reaction force. An accurate measurement of the foot sole pressure directly below is required, but since a position of the action point changes according to a size of a bone of a subject, for example, a small-size round pressure sensor installed at a fixed point may deviate from a center of an action point. Furthermore, this action point often shifts according to a speed, a direction, an inclination, and the like of running or walking, which causes an error in measurement.

In response to this problem, sensors that measure a two-dimensional pressure distribution or sensors that have many pressure-sensing points have been used in a foot sole pressure measurement device. However, there are problems such as an increase in size of a detection circuit, an increase in weight, a short lifetime due to a complicated sensor part, or a high failure frequency, and such foot sole pressure measurement devices have not become widespread. In particular, enlarging an area of the sensor part may cause a change in shape due to an impact such as landing, flexion and extension of the legs, and a reception of stress in a lateral or front-rear direction at the time of stepping down because many pressure sensors have characteristics of causing errors due to bending or pulling stress, and thus there is a defect in that an error occurs in the measurement of a foot sole pressure.

It is important to improve a force and a stride required for jumping at the time of running to enhance a running ability of a player who is a subject. According to a measurement using an instrument for measuring a foot sole pressure, a foot sole pressure at the time of running on a sloping road is increased by 1.1 to 3 times. At the time of running on a sloping road, it can be confirmed that a higher foot sole pressure (force) is required than when running on a flat road.

It is essential to set a gradient and a running speed according to the ability of a runner in running training on a sloping road, but these adjustments are empirically performed, and determination of appropriate setting values for the measurement of a foot sole pressure is an issue.

To measure a foot sole pressure distribution more accurately, many sensors with small areas are disposed over an entire sole to measure a detailed pressure distribution in a device for measuring a foot sole pressure. However, with such a structure, a system is complicated and the number of signal channels is also large, and data processing becomes more complicated. At the same time, since the cost increases and the replacement of a sensor is not easy, this device for measuring a foot sole pressure does not have sufficient performance as a measurement instrument to be used in the field of competition or in daily life.

An enlarged sensor causes distortion in the shape of a sensor and partial bending or stretching due to deformation of a sole or action of complicated forces at the time of running exercise, and causes a large error in the characteristics of a sensor. On the other hand, reducing a sensor size is advantageous in terms of suppressing the error described above, but since a measurement area decreases, this may cause occurrence of a new error such as a sensor deviating from a maximum pressure point and having a reduced sensitivity.

As described above, in conventional technology, there is a problem in that a burden is imposed on a subject or a measurer when an exercise intensity of walking or running is measured.

In view of the above circumstances, an object of the present invention is to provide a technology capable of measuring an exercise intensity of walking or running without imposing a burden on a subject or a measurer.

Means for Solving the Problems

According to one aspect of the present invention, a foot sole pressure measurement instrument includes a measurement unit which is installed on a foot sole part of a subject and measures a pressure applied to the foot sole part of the subject, and an output unit configured to output data of the measured pressure.

In the foot sole pressure measurement instrument according to one aspect of the present invention, it is preferable that the measurement unit be installed on or near a part at which a pressure is twice or more an average value of pressure applied per unit area of the foot sole part.

In the foot sole pressure measurement instrument according to one aspect of the present invention, it is preferable that the measurement unit include a pressure-sensing unit configured to sense a pressure contact, and a shape of the pressure-sensing unit be strip with different aspect ratios.

In the foot sole pressure measurement instrument according to one aspect of the present invention, it is preferable that the pressure-sensing unit be disposed in a longitudinal direction of bones of at least one of a big toe ball, a little toe ball, and a calcaneal portion of the foot sole part of the subject.

According to another aspect of the present invention, an information provision device includes the foot sole pressure measurement instrument, and an information provision unit configured to determine an indicator of running stability based on a fluctuation in foot sole pressure when the subject is running on the basis of the data of the pressure measured by the foot sole pressure measurement instrument, and to provide load information in accordance with an ability of the subject according to the determined indicator.

In the information provision device according to another aspect of the present invention, it is preferable to further include a calculation unit configured to perform a predetermined calculation on the basis of the data of the pressure measured by the foot sole pressure measurement instrument, and a display unit configured to display information based on a result of the calculation performed by the calculation unit.

According to still another aspect of the present invention, an information provision method includes an exercise load information provision step of determining an indicator of running stability based on a fluctuation in foot sole pressure when the subject is running on the basis of the data of the pressure measured by the foot sole pressure measurement instrument, and of providing load information in accordance with the ability of the subject according to the determined indicator.

Advantageous Effects of the Invention

According to the present invention, it is possible to measure an exercise intensity of walking or running without imposing an excessive burden on a subject or a measurer.

EMBODIMENTS FOR CARRYING OUT THE INVENTION

Figure 1:
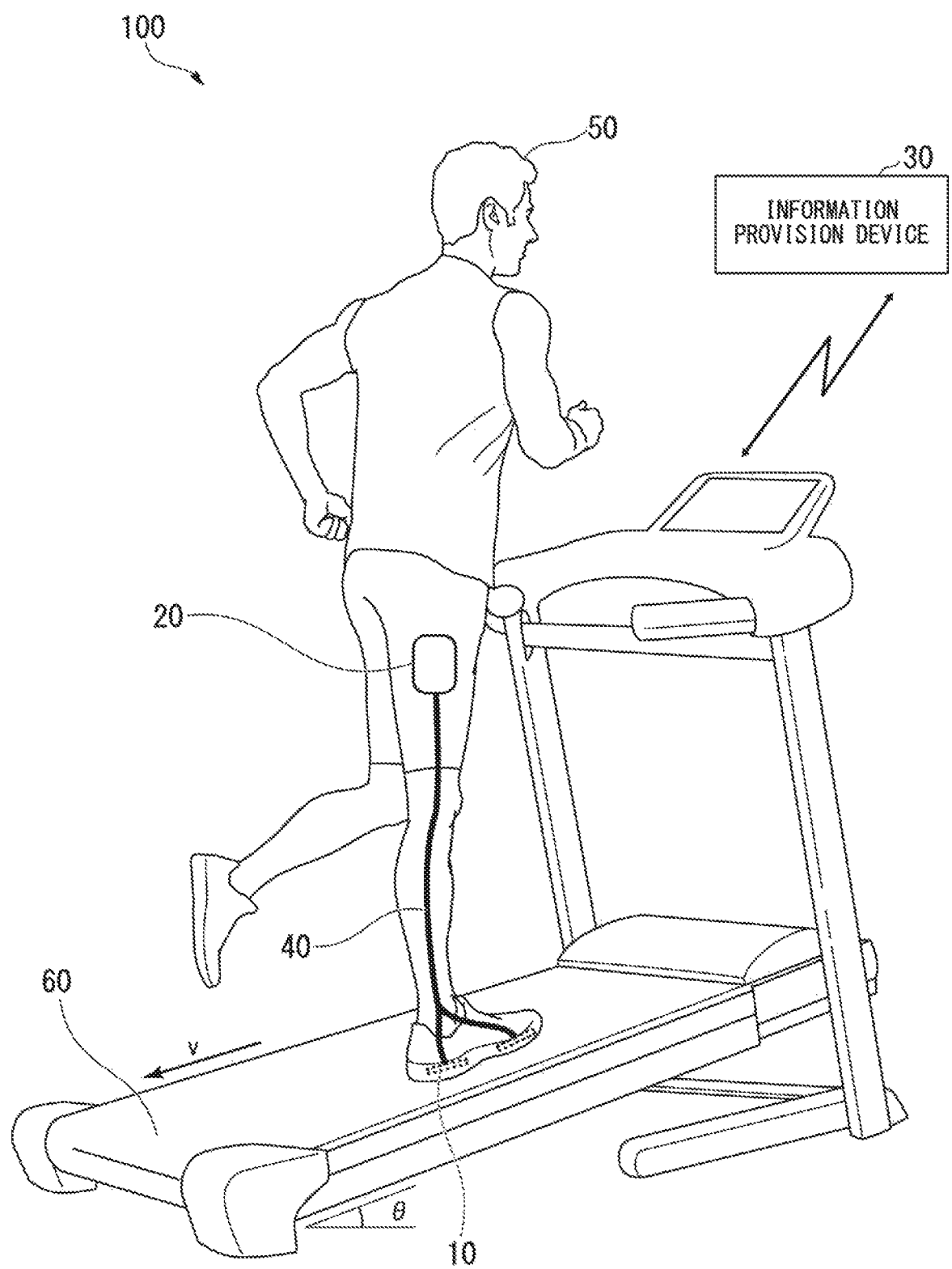
FIG. 1 is a perspective view illustrating an information provision system according to an embodiment of the present invention.

FIG. 1 is a system configuration diagram of an information provision system 100. The information provision system 100 includes one or a plurality of foot pressure sensors 10 (measurement units of a foot sole pressure), a relay device 20 (an output unit), an information provision device 30, and a load-applying device 60. The foot pressure sensor 10 and the relay device 20 are connected via a wired cable 40. In addition, the relay device 20 and the information provision device 30 perform communication using wired communication or wireless communication.

The foot pressure sensor 10 is installed on a foot sole part of a subject 50. Here, the subject is a person who is a target for measurement of exercise intensity during walking or running. The foot pressure sensor 10 measures a pressure (hereinafter, referred to as a "foot sole pressure") applied to the foot sole part of the subject. The foot pressure sensor 10 transmits a result of the measurement (a measured foot sole pressure) to the relay device 20 via the wired cable 40.

The relay device 20 receives the result of the measurement transmitted from the foot pressure sensor 10. The relay device 20 transmits the received result of the measurement to the information provision device 30.

The information provision device 30 is configured using an information processing device such as a personal computer.

The information provision device 30 calculates a standard deviation and the like of a peak value (a maximum foot sole pressure) of a foot sole pressure (force) while the subject 50 is walking or running on the basis of a result of the measurement transmitted from the relay device 20, and displays a result of the calculation. In addition, the information provision device 30 provides information (hereinafter, referred to as "load information") for providing a load in accordance with an ability of the subject. Here, the load information is, for example, information on an inclination angle θ and a running speed v of the load-applying device 60. In addition, the information provision device 30 sets a fluctuation in foot sole pressure at the time of running as an indicator of running stability, and determines an endurance exercise capacity of a subject, a running technique skill, and a degree of fatigue of a subject in accordance with continuation of exercise or a running method (full-speed running or constant speed running such as a marathon) of the subject.

The load-applying device 60 is a device that applies a load to a subject. The load-applying device 60 assists, for example, walking and running on a treadmill, a room runner, and a stepper. The load-applying device 60 can adjust an angle θ and the running speed v of a conveyor belt.

Next, a configuration and an installation method of the foot pressure sensor 10 will be described using FIGS. 2A to 2D.

Figure 2A:
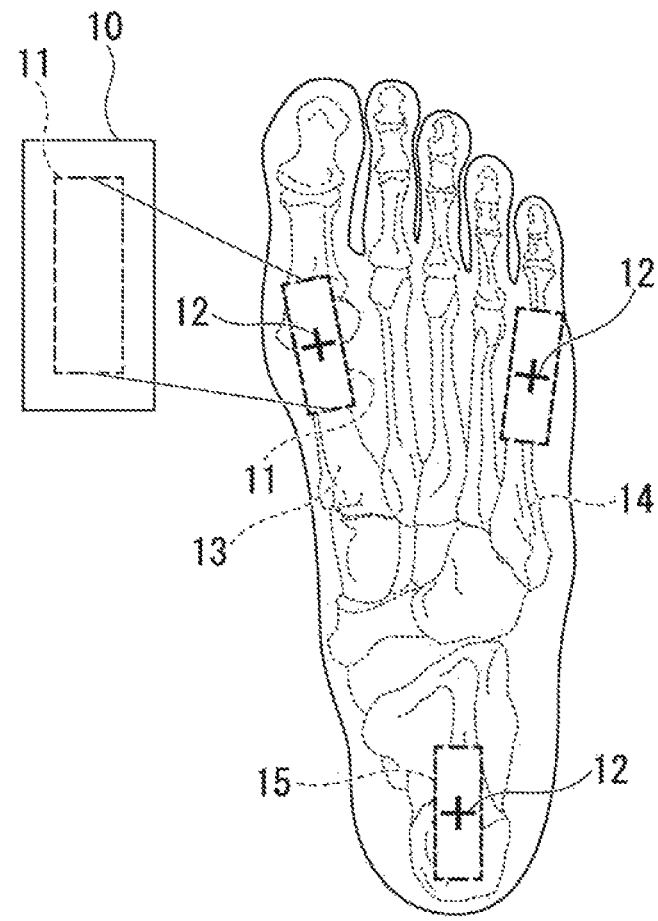
FIG. 2A is a plan view illustrating a configuration of a foot pressure sensor in the embodiment.

As shown in FIG. 2A, the foot pressure sensor 10 is a rectangular plan-type constituent, and is installed on or near a part of the foot sole part at which the pressure is equal to or larger than a threshold. For example, the foot pressure sensor 10 is installed on or near a part (a pressure concentration portion) at which a pressure is twice or more an average value of pressure applied per unit area of the foot sole part. The pressure concentration portion is, for example, a portion at which a big toe ball 13, a little toe ball 14, and a heel bone 15 are located.

The foot pressure sensor 10 adheres to the part at which the big toe ball 13, the little toe ball 14, and the heel bone 15 of the foot sole part of the subject are located. In addition, the foot pressure sensor 10 may be attached to the foot sole part in which the big toe ball 13, the little toe ball 14, and the heel bone 15 are located in socks worn by the subject. Furthermore, the foot pressure sensor 10 may be attached to insoles of athletic shoes in which the big toe ball 13, the little toe ball 14, and the heel bone 15 are located.

In FIG. 2A, an area indicated by a dotted line in the foot pressure sensor 10 is a pressure-sensing unit 11 of the sensor. The pressure-sensing unit 11 senses a pressure using pressure contact. The pressure-sensing unit 11 has a long strip shape with an aspect ratio of 1:2 or more. In FIG. 2A, the foot pressure sensor 10 is provided in three places in the foot sole part of the subject 50, but the foot pressure sensor 10 may be provided in at least one place. In addition, a part 12 indicated by + in the pressure-sensing unit 11 represents a center of a pressure applied to an inside of the pressure-sensing unit 11.

Figure 2B:
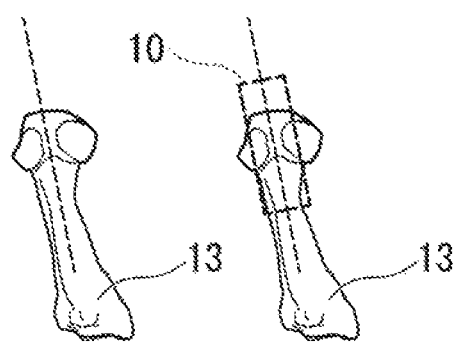
FIG. 2B is a plan view illustrating an example of a disposition position of the foot pressure sensor in the embodiment.
Figure 2C:
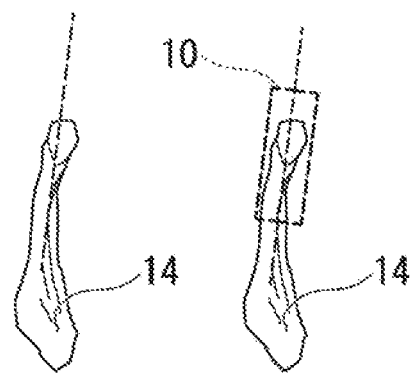
FIG. 2C is a plan view illustrating another example of the disposition position of the foot pressure sensor in the embodiment.
Figure 2D:
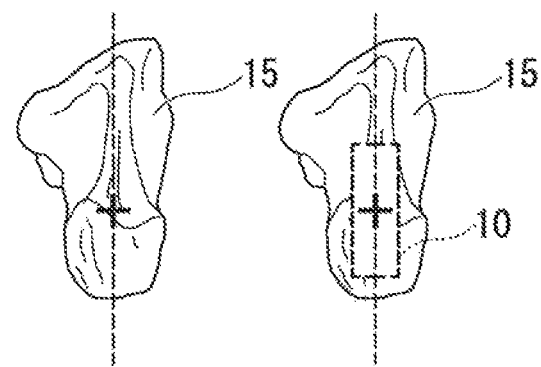
FIG. 2D is a plan view illustrating still another example of the disposition position of the foot pressure sensor in the embodiment.

FIG. 2B shows an example in which the foot pressure sensor 10 is disposed along a metatarsal bone located at the big toe ball 13. FIG. 2C shows an example in which the foot pressure sensor 10 is disposed along a metatarsal bone located at the little toe ball 14. FIG. 2D shows an example in which the foot pressure sensor 10 is disposed along the heel bone 15.

As shown in FIGS. 2B to 2D, the foot pressure sensor 10 is anatomically disposed in a longitudinal direction of bones (heel bone, metatarsal bone, toe bone) of the foot. In addition, the foot pressure sensor 10 includes an adjusting unit. The adjusting unit adjusts a gain and a base line of an amplifier for an analog signal of the pressure-sensing unit when change in sensitivity due to individual differences in pressure distribution, wearing of the pressure-sensing unit of the foot pressure sensor 10, or the like is equal to or more than a threshold. In addition, the adjusting unit adjusts the gain or base line of an amplifier by signal processing after analog to digital conversion.

Figure 3A:
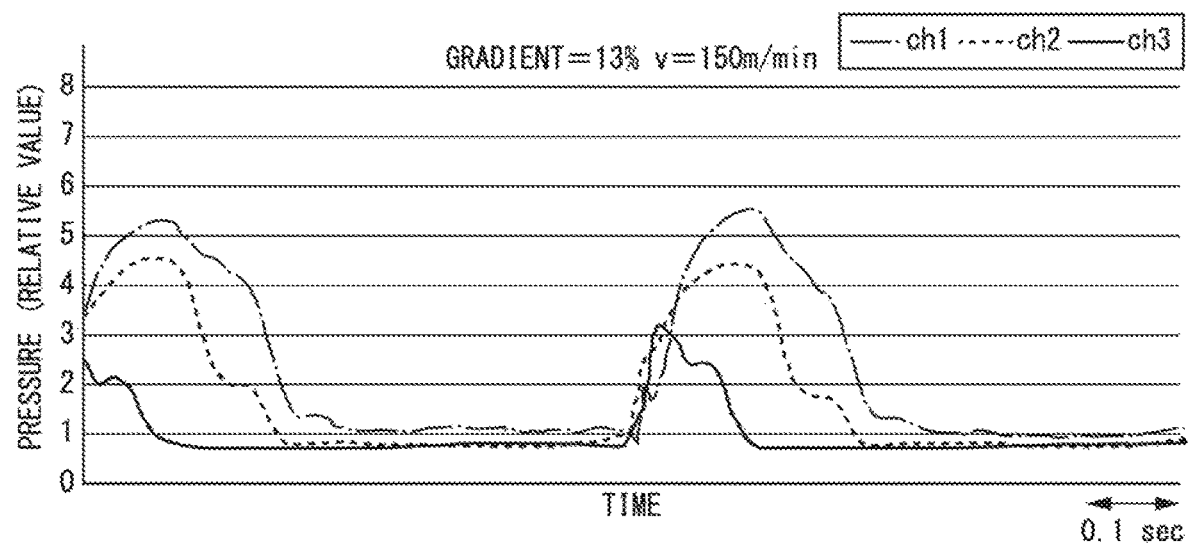
FIG. 3A is a graph illustrating a measurement example of change with time in foot sole pressure (force) at a position of each foot pressure sensor in the embodiment.
Figure 3B:
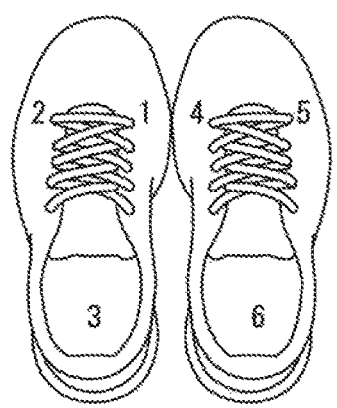
FIG. 3B is a plan view illustrating the disposition position of the foot pressure sensor in the embodiment.

FIG. 3A is a graph which indicates a measurement example of change with time in the foot sole pressure (force) at a position of each foot pressure sensor 10 at the time of running with the foot pressure sensor 10 attached. In addition, FIG. 3B is a diagram which shows the position of the foot pressure sensor 10. Regarding measurement conditions for results of the measurement shown in FIG. 3A, the load-applying device 60 is inclined by 13% and the subject 50 is caused to run at a running speed of 150 m/min. At this time, as shown in FIG. 3B, three foot pressure sensors 10 are attached to the foot sole part of both feet of the subject 50. ch1, ch2, and ch3 in FIG. 3A indicate a result of measuring the foot sole pressure (force) by disposing the foot pressure sensors 10 at positions 1, 2, and 3 in FIG. 3B, respectively. For example, ch1 in FIG. 3A indicates a result of measuring the foot sole pressure (force) by disposing the foot pressure sensor 10 at the position 1 in FIG. 3B.

Figure 4A:
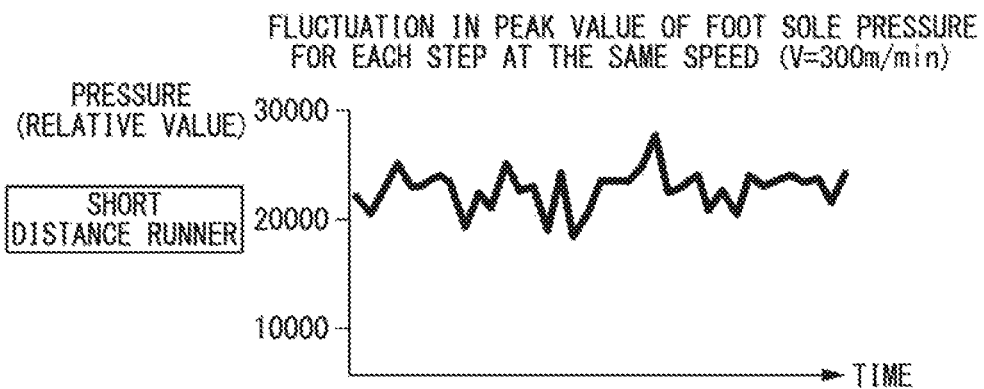
FIG. 4A is a graph illustrating an example of change with time in peak value of a foot sole pressure in the embodiment.
Figure 4B:
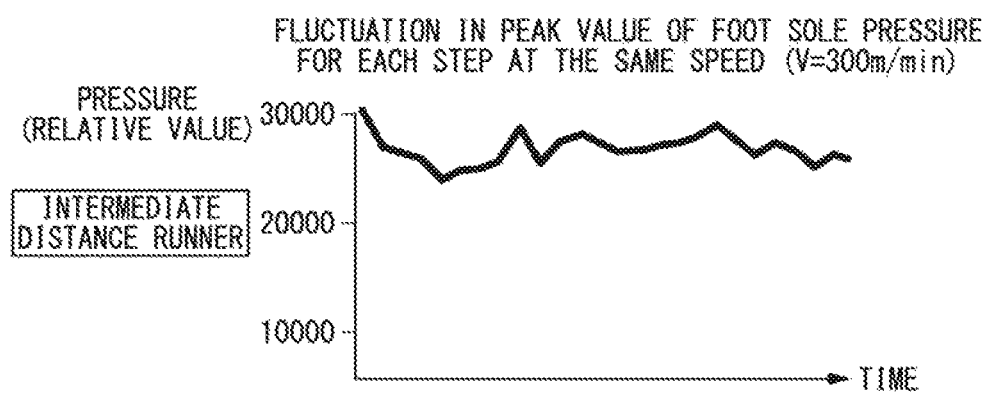
FIG. 4B is a graph illustrating another example of change with time in peak value of a foot sole pressure in the embodiment.
Figure 4C:
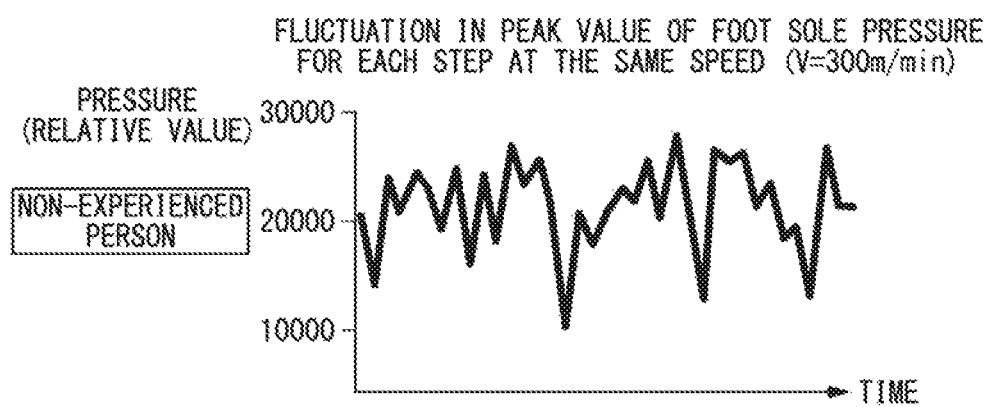
FIG. 4C is a graph illustrating still another example of change with time in peak value of a foot sole pressure in the embodiment.

FIGS. 4A, 4B, and 4C are diagrams which show change in the peak value of the foot sole pressure (force) of a short distance runner, an intermediate distance runner, and a non-experienced person, respectively. As shown in FIGS. 4A, 4B, and 4C, a magnitude of the fluctuation in the peak value of the foot sole pressure (force) varies depending on a runner and a running state, and can be used as an indicator of stability of running.

That is, in the case of the short distance runner shown in FIG. 4A, a variation in the foot sole pressure (ground pressure) for each step is seen, and the stability of running is slightly low. Therefore, it can be said that this short distance runner has an exercise efficiency which is not very good. In the case of the intermediate distance runner shown in FIG. 4B, there is almost no variation in the foot sole pressure (ground pressure) for each step, and the stability of running is very high. Therefore, it can be said that this intermediate distance runner has a high exercise efficiency. In the case of the non-experienced person in athletics shown in FIG. 4C, the variation in the foot sole pressure (ground pressure) for each step is large, and the stability of running is low. Therefore, it can be said that this non-experienced person has a poor exercise efficiency.

In this manner, it can be said that the intermediate distance runner who requires high-efficiency running exercise has less fluctuation in foot sole pressure (ground pressure) as shown in FIG. 4B, and the non-experienced person has a large fluctuation in foot sole pressure (ground pressure) and low stability as shown in FIG. 4C. In addition, it can be said that the short distance runner who exerts full power in a short time has a slightly large fluctuation in the foot sole pressure (ground pressure), and is somewhat unstable as shown in FIG. 4A. That is, it is clear that the foot sole pressure at the time of contact with the ground is maintained in a stable estate in intermediate and long distance running in which exercise is continued for a long time to some extent.

The intermediate distance runner has higher efficiency in running exercise than the non-experienced person and the short distance runner. As shown in FIG. 4B, the peak value (maximum foot sole pressure) of the foot sole pressure when the intermediate distance runner is grounded is constant. On the other hand, as shown in FIG. 4A, in the case of the short distance runner, the peak value of the foot sole pressure at the time of contact with the ground is unstable, and strength of the peak value at each step is recognized. Furthermore, as shown in FIG. 4C, in the case of the non-experienced person, the peak value of the foot sole pressure at the time of contact with the ground is more unstable, and the strength of the peak value at each step becomes more prominent. That is, the efficiency of running exercise is higher, and the fluctuation (variation) in the peak value of the foot sole pressure when the intermediate distance runner is grounded is less. The information provision device 30 evaluates the efficiency and skill of running exercise using the fluctuation (variation) in the peak value (maximum foot sole pressure) of the foot sole pressure at the time of contact with the ground.

An exercise intensity at which the fluctuation (variation) in the peak value (maximum foot sole pressure) of the foot sole pressure at the time of contact with the ground described above increases is correlated with an exercise intensity of a lactic acid threshold (lactate threshold). Accordingly, the lactate threshold can be estimated by gradually increasing the exercise intensity and detecting an increase in the fluctuation (variation) of the peak value (maximum foot sole pressure) of the foot sole pressure at the time of contact with the ground as a change point.

The change with time in the foot sole pressure at the time of running is measured, and, as an indicator of running stability, the fluctuation in the peak value of the foot sole pressure (force) in repeated landing and jumping operations is used as a feature value. As the running speed increases, the foot sole pressure (force) at sole surfaces increases, and accordingly, the fluctuation in the peak value of the foot sole pressure gradually increases. The magnitude of the fluctuation is an indicator of the skill of the running technique of the subject. At the same time, a large fluctuation in the peak value of the foot sole pressure indicates that a training intensity for the subject is higher than an optimum intensity. The fluctuation in the peak value of the foot sole pressure changes with time due to running for a long time, and can be used as an indicator of the progress of fatigue of a runner.

Various indicators used in statistical processing can be used to calculate the fluctuation (variation) in the peak value of the foot sole pressure (force). The various indicators include, for example, a standard deviation, a variance, a standard error, a range, an interquartile range, an average difference, an average absolute deviation, and the like. In addition, data may be normalized when necessary in a calculation process of these indicators.

Training on slopes (treadmills with slopes) is known to be more efficient running training. According to a result of measurement using the foot pressure sensor 10, the foot sole pressure at the time of running on a sloping road is 1.1 to 3 times higher compared to that of running on flat ground, and a higher force is exerted. In order to improve running exercise ability, it is regarded important to acquire a larger stride, and it is recommended to exert a greater force. The result of the measurement described above indicates that running exercise on slopes requires an exertion of a greater force than running exercise on flat ground, and suggests that running exercise on slopes is effective training after acquiring a larger stride.

Figure 5:
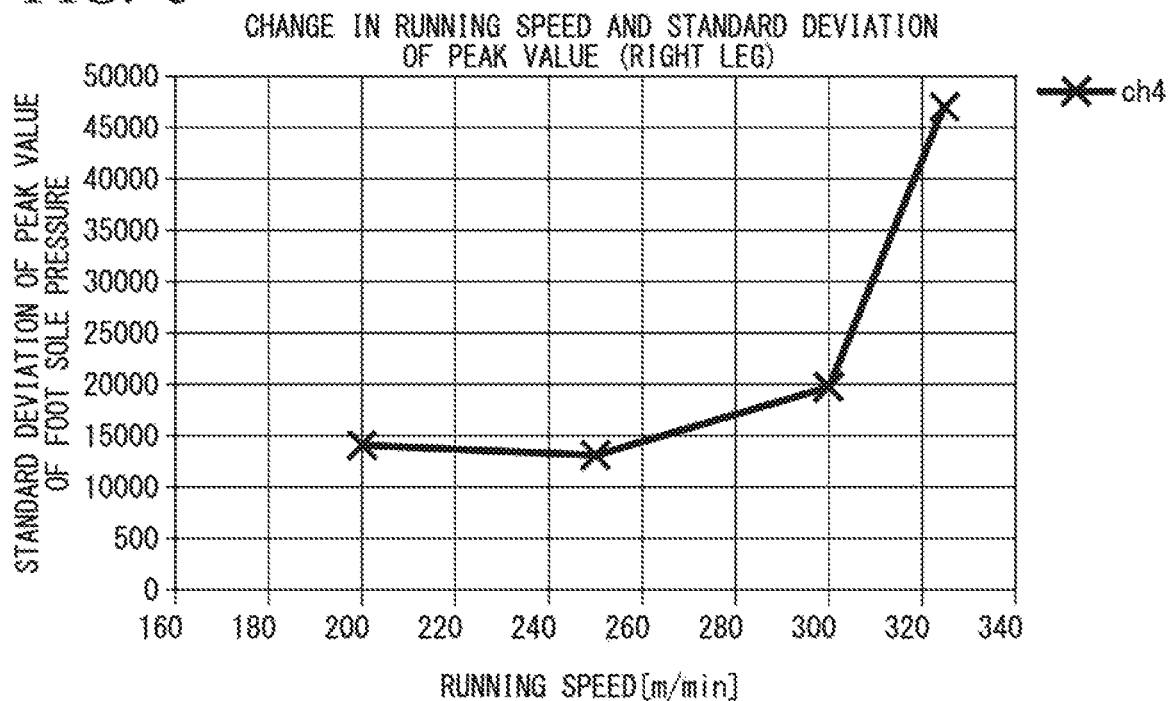
FIG. 5 is a graph illustrating a running speed and change in standard deviation of the peak value of a foot sole pressure in the embodiment.

FIG. 5 is a diagram which shows a running speed and change in standard deviation of the peak value of the foot sole pressure in the big toe ball (a position 4 of FIG. 3B). FIG. 5 shows a degree (a standard deviation of the peak value of the foot sole pressure at a certain running speed) of the fluctuation of the peak value of the foot sole pressure when the running speed of a certain runner is increased. As the running speed increases, a load on the runner increases and the runner enters a more difficult state. The standard deviation of the peak value of the foot sole pressure has a tendency to increase as the running speed increases (big toe ball (the position 4 of FIG. 3B)), and shows a shift to an unstable state in which the fluctuation in the peak value of the foot sole pressure is large at a running speed of 300 m/min or higher.

Figure 6:
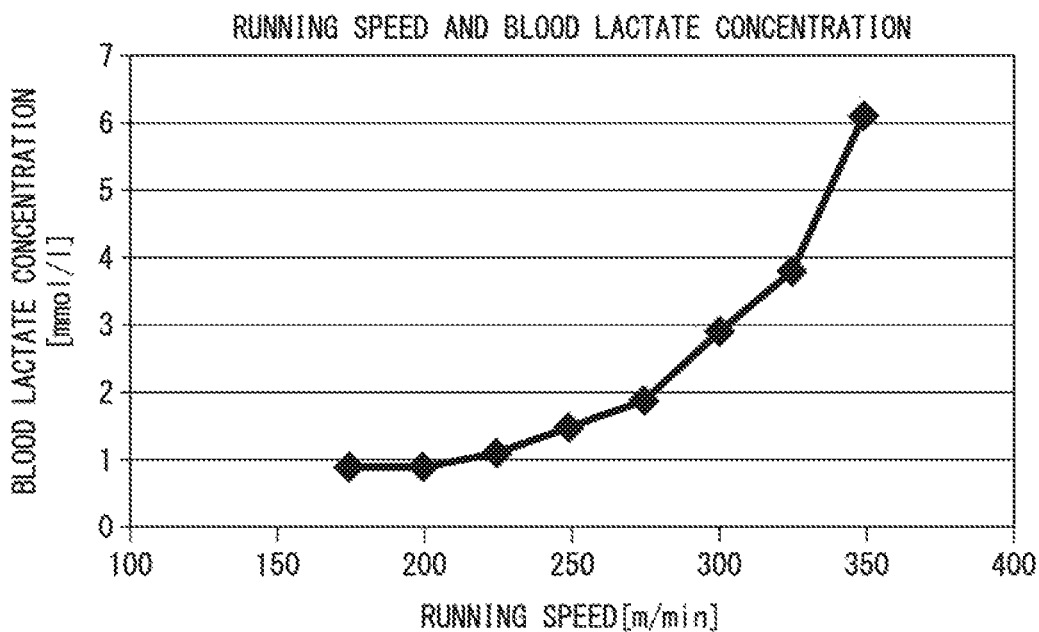
FIG. 6 is a graph illustrating a relationship between the running speed and a blood lactate concentration in the embodiment.

A change in the magnitude of the fluctuation in the peak value of the foot sole pressure also corresponds to an increase in blood lactate concentration measured simultaneously at a running speed of 260 to 300 m/min or higher. That is, in FIG. 6, the blood lactate concentration at a running speed of 325 m/min or higher becomes a state of 4 mmol/l or higher in which it is difficult for the runner to maintain running for a long time. This shows that the fluctuation in the peak value of the foot sole pressure at the time of running corresponds to difficulty for the runner. That is, the fluctuation in the peak value of the foot sole pressure becomes large in a load that causes difficulty for the runner. While the running speed is low and running is stable, the fluctuation of the peak value is also maintained to be low (FIG. 5).

In addition, the lactate threshold can be determined non-invasively using such a property of the fluctuation of the peak value of the foot sole pressure. The runner can determine whether the exercise intensity is too high or too low, and the lactate threshold can be used as an indicator for setting an optimum exercise intensity.

Figure 7A:
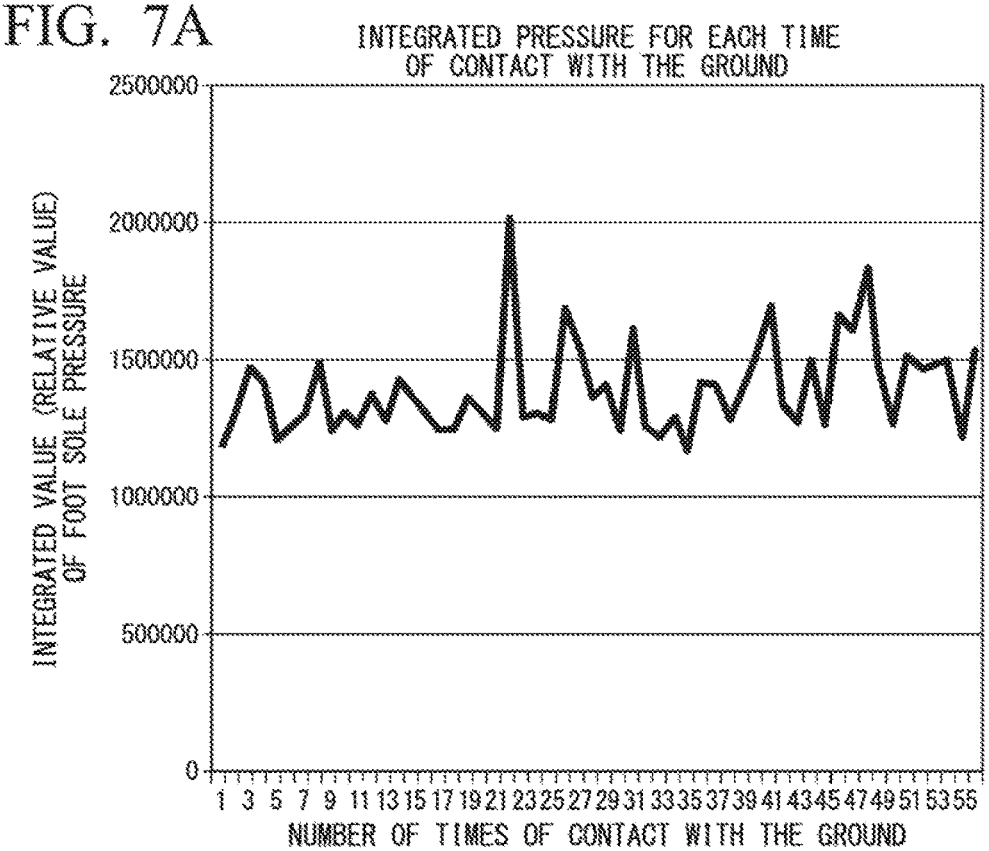
FIG. 7A is a graph illustrating a relationship between the number of times a runner's foot comes into contact with the ground in running on a sloping road and an integrated value of a foot sole pressure for each contact with the ground in the embodiment.
Figure 7B:
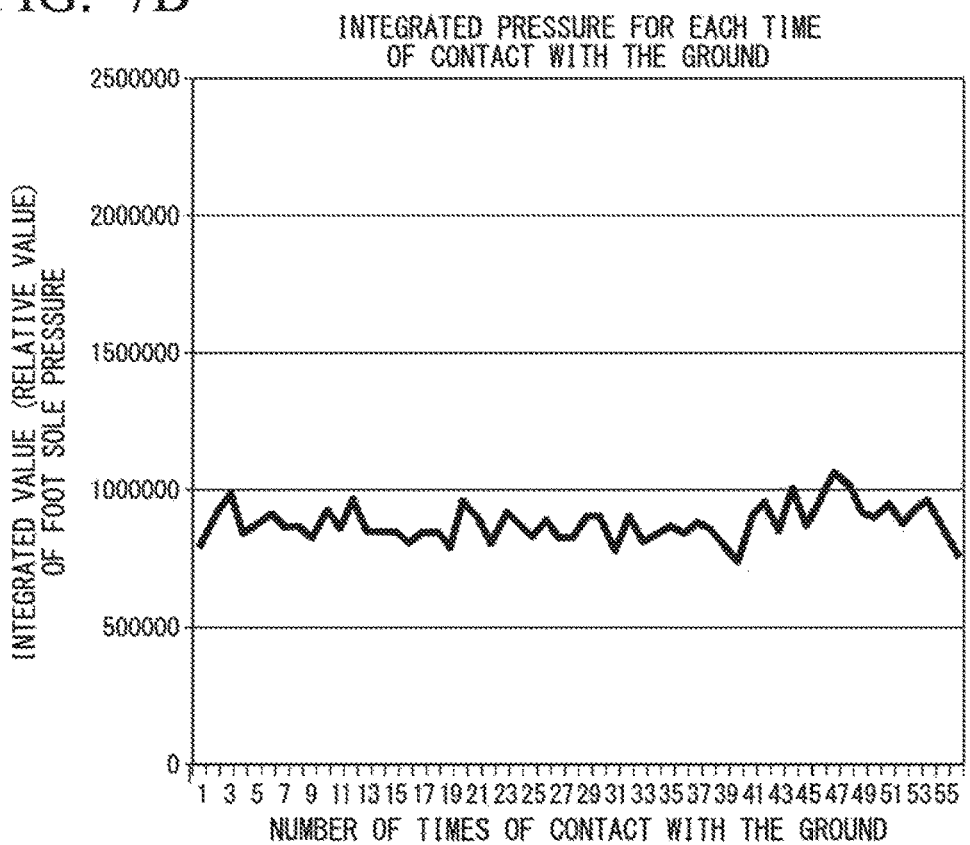
FIG. 7B is a graph illustrating a relationship between the number of times a runner's foot comes into contact with the ground in running on flat ground and an integrated value of a foot sole pressure for each contact with the ground in the embodiment.

FIGS. 7A and 7B are diagrams which show an increase in an amount of exercise load due to running on a sloping road measured by the information provision system 100. In FIGS. 7A and 7B, the horizontal axis represents the number of times of contact with the ground by the runner, and the vertical axis represents an integrated pressure for each time of contact with the ground. This integrated pressure is a value obtained by adding values of foot sole pressures measured in a certain sampling period for each time of contact with the ground. FIG. 7A shows an integrated pressure for each time of contact with the ground in running on a sloping road, and FIG. 7B shows an integrated pressure for each time of contact with the ground in running on flat ground. As shown in FIG. 7A, the average of the integrated pressure of foot sole pressures at all times of contact with the ground in running on a sloping road is about 1.5 times higher than the average of the integrated pressure of foot sole pressures at all times of contact with the ground in running on flat ground, as shown in FIG. 7B.

A foot sole pressure (force) and a pitch can be measured at the same time by the foot pressure sensor 10. The information provision device 30 determines a gradient and a speed of the load-applying device 60 to achieve an optimum foot sole pressure (force) in accordance with the ability of the subject, and a pitch, provides these to the load-applying device 60, and provides the subject with more effective training. For example, beginners respond by increasing the pitch more than the stride as the running speed increases, but, if the pitch reaches a certain degree or more, the fluctuation in the peak value of the foot sole pressure (force) increases, and a tendency to decrease the efficiency of running exercise is recognized.

For this reason, the information provision device 30 provides information (the gradient and speed of the load-applying device 60, and the pitch of the subject) which enables a highly efficient and stable running exercise based on a changing point at which the fluctuation of the peak value of the foot sole pressure increases, whereby practicing more effectively and learning to run marathons without withdrawals or weakening is able to be achieved.

In addition, an intermediate runner can increase a force by gradually raising an inclination angle θ while observing the peak value of the foot sole pressure (force) and perform a reinforcement exercise for enabling a larger stride to improve performance by improving the efficiency of running exercise. In this case, since exercises with an excessive inclination angle θ or pitch reduce the efficiency of running exercise and induce sudden fatigue, an efficient reinforcement exercise can be performed by exercising with a load which suppresses the fluctuation of the peak value of the foot sole pressure (force) within a range of not exceeding a predetermined magnitude.

For an advanced runner, it is possible to provide an effective training method with more accuracy than a training method on flat roads in the prior art. Furthermore, since it is possible to ascertain how an influence of force, running exercise, and fatigue changes when running with a varied stride or pitch, such as force measurement in various scenes in a real field, overtaking, or jumping out, is implemented using the load-applying device 60 as numerical values instead of a sensory manner, self-feedback, training with high reproducibility, and competition simulation are possible.

Figures 8, 9:
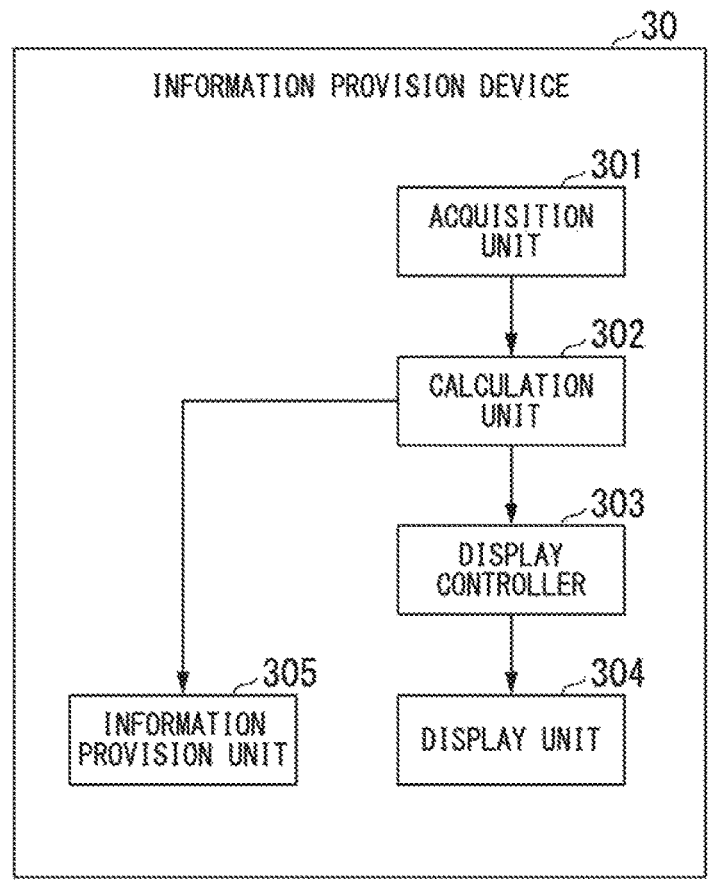
FIG. 8 is a table illustrating a result of comparing a relationship between a pitch, a stride, and a blood lactate concentration in running on flat ground and running on a sloping road in the embodiment.
FIG. 9 is a block diagram illustrating an information provision device in the embodiment.

FIG. 8 is a diagram which shows a comparison result in a relationship between the pitch, stride, and blood lactate concentration between running on flat ground and running on a sloping road. As shown in FIG. 8, if running on flat ground and a slope at a running speed v=200 m/min are compared, the pitch increases (gets higher), the stride becomes shorter, and the blood lactate concentration rises in the case of the sloping load running compared with the case of running on flat ground. When running on flat ground and a slope at a running speed v=225 m/min are compared, the pitch increases, the stride becomes shorter, and the blood lactate concentration significantly rises in the case of the sloping load running compared with the case of running on flat ground. When the stride becomes longer, the foot sole pressure (force) is higher. That is, the foot sole pressure (force) becomes higher and the blood lactate concentration also rises in running on a sloping road, and a higher load is applied to a runner.

Training focusing on force (stride) improvement can be implemented by restricting the pitch with respect to an increase in running speed, instructing maintaining a speed by increasing a force (maintaining or increasing the stride), and efficiently improving the force in training based on the points described above.

Since the information provision device 30 can measure the force and the pitch, it is possible to devise an appropriate combination of the gradient, running speed, force, and pitch of the load-applying device 60 in accordance with the ability of a player, and to perform efficient guidance.

For example, the information provision device 30 may provide information of the pitch 160 at the gradient 3% and the speed v=200 m/min to the subject (runner) serving as a measurement target in FIGS. 5 to 8. If the subject performs training under conditions based on the provided information, the foot sole pressure can be increased by a factor of 1.5 times and an appropriate exercise intensity can be obtained to improve the force (stride) of the subject.

FIG. 9 is a schematic block diagram which represents a functional configuration of the information provision device 30.

The information provision device 30 includes a central processing unit (CPU), a memory, an auxiliary storage device, and the like connected by a bus, and executes a provision program. According to the execution of the provision program, the information provision device 30 functions as a device which includes an acquisition unit 301, a calculation unit 302, a display controller 303, a display unit 304, and an information provision unit 305. Note that all or some of the functions of the information provision device 30 may be realized using hardware such as an application-specific integrated circuit (ASIC), a programmable logic device (PLD), or a field-programmable gate array (FPGA). In addition, the provision program may also be recorded in a computer-readable recording medium. The computer-readable recording medium is, for example, a portable medium such as a flexible disk, an optical magnetic disc, a ROM, or a CD-ROM, and a storage device such as a hard disk embedded in a computer system. In addition, the provision program may be transmitted or received via a telecommunication line.

The acquisition unit 301 acquires a result of the measurement measured by the foot pressure sensor 10 from the relay device 20. The acquisition unit 301 outputs the acquired result of the measurement to the calculation unit 302.

The calculation unit 302 performs a predetermined calculation on the measurement results output from the acquisition unit 301. Here, the predetermined calculation is, for example, a standard deviation, a variance, a standard error, a range, an interquartile range, an average difference, an average absolute deviation, and the like. The display controller 303 causes the display unit 304 to display information on the basis of a result of the calculation. For example, the display controller 303 causes the display unit 304 to display the graphs shown in FIGS. 5 to 8.

The display unit 304 is an image display device such as a liquid crystal display or an organic electro luminescence (EL) display. The display unit 304 may also be an interface for connecting an image display device to the information provision device 30. In this case, the display unit 304 generates a video signal for displaying information, and outputs the video signal to an image display device connected thereto.

The information provision unit 305 sets a fluctuation in the foot sole pressure at the time of running obtained on the basis of measurement data of the pressure as an indicator of running stability, determines the endurance exercise capacity of a subject, the skill of a running technique, and the degree of fatigue of a subject in accordance with continuation of exercise or a running method (full-speed running or constant speed running such as a marathon) of the subject, and provides load information in accordance with the ability of a subject according to a result of the determination. The information provision unit 305 holds a determination table. The determination table is a table used to determine a state of the subject 50 at the time of exercising. In the determination table, a fluctuation in the foot sole pressure at the time of running and information on a determination target (the endurance exercise capacity of a subject, the skill of a running technique, the degree of fatigue of the subject in accordance with continuation of exercise, and a running method of the subject) are associated with each other. That is, states of the endurance exercise capacity of a subject, the skill of a running technique, the degree of fatigue of the subject in accordance with continuation of exercise, and a running method of the subject are determined in accordance with the fluctuation in the foot sole pressure at the time of running. The information provision unit 305 refers to the determination table and determines the endurance exercise capacity of a subject, the skill of a running technique, the degree of fatigue of the subject in accordance with continuation of exercise, or a running method of the subject in accordance with the fluctuation obtained on the basis of the measurement data of the pressure. Note that it is not necessary that all determination targets be associated with the fluctuation of the foot sole pressure at the time of running, and only some of the determination targets may be associated in the determination table. In addition, the determination targets may be set for each subject or may be set each time.

In addition, the information provision unit 305 holds a load information table. The load information table is used when load information in accordance with the ability of a subject is determined. In the load information table, a result of determination and load information in accordance with the result of the determination are associated with each other. The information provision unit 305 acquires load information in accordance with the ability of a subject according to a result of the determination with reference to the load information table. Thereafter, the information provision unit 305 provides the acquired load information. For example, the information provision unit 305 may provide load information by causing the display unit 304 to display the load information, provide load information by reading the load information using speech, and provide load information by printing the load information.

In addition, the information provision unit 305 evaluates the efficiency and skill of running exercise according to a deviation (variation) of the peak value (maximum foot sole pressure) of the foot sole pressure at the time of contact with the ground. For example, the information provision unit 305 may evaluate that the efficiency and skill of running exercise are very poor when the deviation (variation) of the peak value (maximum foot sole pressure) of the foot sole pressure at the time of contact with the ground is equal to or greater than a first threshold. In addition, for example, the information provision unit 305 evaluates that the efficiency and skill of running exercise are poor when the deviation (variation) of the peak value (maximum foot sole pressure) of the foot sole pressure at the time of grounding is equal to or greater than a second threshold value smaller than the first threshold value, and is smaller than the first threshold. In addition, for example, the information provision unit 305 evaluates that the efficiency and skill of running exercise are good when the deviation (variation) of the peak value (maximum foot sole pressure) of the foot sole pressure at the time of contact with the ground is smaller than the second threshold.

According to the information provision system 100 configured as described above, exercise information can be measured non-invasively. Specifically, in the information provision system 100, the foot pressure sensor 10 is installed in the foot sole part of a subject, and measures a pressure applied to the foot sole part of a subject. As a result, the subject only needs to walk or run. For this reason, it is possible to measure exercise information non-invasively.

The information provision system 100 can expand a width corresponding to a variation in the size of the bone by installing the foot pressure sensor 10 with a different aspect ratio. In addition, since a direction in which a foot sole force is applied is mainly inclined to a longitudinal axis (close to a long axis of the bone) due to a change in a state of running or walking by taking a short side of the pressure-sensing unit slightly wider (for example, a width of 0.5 to 1.0 cm), stable measurement with respect to a change of state can be realized. In a design of the foot pressure sensor 10, an error caused by the above-described shape distortion with a large sensor can be avoided by using a sensor corresponding to bending in one direction.

According to the shape of the foot pressure sensor 10 described above, it is possible to make a pressure-sensing area wider than that of a conventional sensor, to reduce the number of sensors by optimizing a range covered by the pressure-sensing unit 11 and disposition places, and to respond to areas of foot sole parts having individual differences, a pressure distribution, a deformation of a foot sole part due to a change in gait, and a change in a direction of force. Furthermore, sensor replacement and sensitivity adjustment can be simplified for durability issues or sensor sensitivity fluctuation due to mechanical stress according to running exercise.

According to the foot pressure sensor 10 described above, it is possible to ascertain a precise running situation while actually running in the field as well as in a laboratory. This is a general-purpose foot sole pressure sensor system which can be used continuously in competition and daily life.

In addition, by using the foot pressure sensor 10, it is possible to accurately measure an increase in the foot sole pressure (force) due to a change in gradient. For this reason, the information provision device 30 can provide exercise information of an optimal foot sole pressure (force) with which a training effect in accordance with the ability of a user is obtained. Then, the subject can perform more effective training by running with settings (for example, a gradient, a running speed, and the like) in accordance with the provided information.

MODIFIED EXAMPLES

Some of the functional units included in the information provision device 30 may also be included in another device. For example, the display unit 304 included in the information provision device 30 may be included in another device (for example, a single display device), and other functional units except for the display unit 304 may also be included in the information provision device 30. In this case, for example, the information provision device 30 is disposed near the subject 50, and the other device including the display unit 304 is disposed in a place (for example, an adjacent room, or the like) spaced apart from a place where the subject 50 is located. With such a configuration, the display controller 303 transmits information to be displayed on the display unit 304 to another device including the display unit 304.

As a result, a measurer can ascertain information of a subject even if the measurer is not near the subject.

The information provision system 100 may also be configured to further include an adjusting unit that adjusts a load amount to an optimum range by changing the running speed or slopes of the load-applying device 60 that assists walking and running of a treadmill, a room runner, and a stepper on the basis of load information of the information provision unit 305 and a past exercise history. The adjusting unit is included in, for example, the load-applying device 60. With such a configuration, the adjusting unit acquires load information from the information provision unit 305. In addition, the adjusting unit holds information on the past exercise history of the subject 50. The information on the past exercise history is, for example, information related to a running speed and a slope when the subject 50 performed an exercise within a predetermined period using the load-applying device 60. Then, the adjusting unit determines the changed running speed and slope of the load-applying device 60 on the basis of the acquired load information and the held past exercise history. For example, the adjusting unit may also determine an average running speed and a slope on the basis of the load information and the held past exercise history. The adjusting unit adjusts the running speed and slope of the load-applying device 60 to be the determined running speed and slope. Note that the adjusting unit may also determine a running speed and a slope using other statistical values (for example, a mode value, a maximum value, and the like) instead of the average running speed and slope as the changed running speed and slope of the load-applying device 60. Furthermore, based on an endurance ability and the past exercise history of the subject, when an exercise load is too small for the subject, the load may be increased gradually to reach an optimum load or increased for a certain period of time during interval running. Conversely, when the exercise load is excessive with respect to the endurance of the subject, the load amount may be reduced gradually or the load amount may also be optimized by giving a uniformly slowing section.

As a result, the load applied to the subject 50 can be dynamically adjusted.

As described above, the embodiments of the present invention have been described in detail with reference to the drawings, but a specific configuration is not limited to these embodiments, and a design and the like within a scope not departing from the gist of the present invention are included.

INDUSTRIAL APPLICABILITY

According to the foot sole pressure measurement device of the present invention, it is possible to measure an exercise intensity of walking or running without giving an excessive burden to a subject or measurer.

REFERENCE SYMBOLS LIST

10 Foot pressure sensor
20 Relay device
30 Information provision device
40 Wired cable
60 Load-applying device
301 Acquisition unit
302 Calculation unit
303 Display controller
304 Display unit
305 Information provision unit

The invention claimed is:

1. A foot sole pressure measurement instrument, comprising:
a measurement unit for installation on a foot sole part of a subject so as to measure a pressure applied to the foot sole part of the subject by a pressure-sensing unit configured to sense a pressure contact, a shape of the pressure-sensing unit being a strip; and
an output unit configured to output data of the measured pressure,
wherein the pressure-sensing unit is configured to be disposed in a location where a bone of at least one of a big toe ball, a little toe ball and a calcaneal portion of the foot sole part of the subject is located such that the pressure sensing unit will be disposed of along a longitudinal direction of the bone, and
wherein the measurement unit includes an adjusting unit configured to adjust a gain and a base line of an amplifier for an analog signal of the pressure-sensing unit by signal processing after analog-to-digital conversion when change in sensitivity due to individual difference in pressure distribution or exhaustion of the pressure sensing unit of the measurement unit is equal to or greater than a threshold.

2. The foot sole pressure measurement instrument according to claim 1, wherein the measurement unit is installed on or near a part at which a pressure is twice or more than an average value of pressure applied to the foot sole part.

3. An information provision device, comprising:
a foot sole pressure measurement instrument including a measurement unit for installation on a foot sole part of a subject so as to measure a pressure applied to the foot sole part of the subject by a pressure-sensing unit configured to sense a pressure contact, a shape of the pressure-sensing unit being a strip, and an output unit configured to output data of the measured pressure, wherein the pressure-sensing unit is configured to be disposed in a location where a bone of at least one of a big toe ball, a little toe ball and a calcaneal portion of the foot sole part of the subject is located such that the pressure-sensing unit will be disposed along a longitudinal direction of the bone, and wherein the measurement unit includes an adjusting unit configured to adjust a gain and a base line of an amplifier for an analog signal of the pressure-sensing unit by signal processing after analog-to-digital conversion when change in sensitivity due to individual difference in pressure distribution or exhaustion of the pressure sensing unit of the measurement unit is equal to or greater than a threshold; and an information provision unit configured to determine an indicator of running stability based on a fluctuation in foot sole pressure when the subject is running on the basis of the data of the pressure measured by the foot sole pressure measurement instrument, and to provide load information in accordance with an ability of the subject according to the determined indicator.

4. The information provision device according to claim 3, further comprising:

a calculation unit configured to perform a predetermined calculation on the basis of the data of the pressure measured by the foot sole pressure measurement instrument; and a display unit configured to display information based on a result of the calculation performed by the calculation unit.

5. An information provision method, comprising:

measuring a data of a pressure by a foot sole pressure measurement instrument including a measurement unit for installation on a foot sole part of a subject so as to measure a pressure applied to the foot sole part of the subject by a pressure-sensing unit configured to sense a pressure contact, a shape of the pressure-sensing unit being a strip, and an output unit configured to output data of the measured pressure, wherein the pressure-sensing unit is configured to be disposed in a location where a bone of at least one of a big toe ball, a little toe ball and a calcaneal portion of the foot sole part of the subject is located such that the pressure-sensing unit will be disposed along a longitudinal direction of the bone, and wherein the measurement unit includes an adjusting unit configured to adjust a gain and a base line of an amplifier for an analog signal of the pressure-sensing unit by signal processing after analog-to-digital conversion when change in sensitivity due to individual difference in pressure distribution or exhaustion of the pressure sensing unit of the measurement unit is equal to or greater than a threshold;

determining an indicator of running stability based on a fluctuation in foot sole pressure when the subject is running on the basis of the data of the pressure; and providing load information in accordance with an ability of the subject according to the determined indicator.

* * * * *